US006841072B2

(12) United States Patent
Vellinga et al.

(10) Patent No.: US 6,841,072 B2
(45) Date of Patent: Jan. 11, 2005

(54) METHOD AND DEVICE FOR THE ANAEROBIC PURIFICATION OF A SLURRY WHICH CONTAINS ORGANIC CONSTITUENTS

(75) Inventors: Sjoerd Hubertus Jozef Vellinga, Tjalleberd (NL); Ronald Mulder, Alkmaar (NL)

(73) Assignee: Paques Bio Systems B.V., Balk (NL)

( * ) Notice: Subject to any disclaimer, the term of this patent is extended or adjusted under 35 U.S.C. 154(b) by 0 days.

(21) Appl. No.: 10/472,895

(22) PCT Filed: Mar. 26, 2003

(86) PCT No.: PCT/NL02/00193

§ 371 (c)(1),
(2), (4) Date: Sep. 25, 2003

(87) PCT Pub. No.: WO02/076893

PCT Pub. Date: Oct. 3, 2002

(65) Prior Publication Data

US 2004/0108267 A1 Jun. 10, 2004

(30) Foreign Application Priority Data

Mar. 26, 2001 (NL) ............................................ 1017690

(51) Int. Cl.[7] .............................. C02F 3/28; C02F 1/24

(52) U.S. Cl. .................... 210/608; 210/629; 210/221.1

(58) Field of Search ................................ 210/603, 608, 210/194, 221.1, 629

(56) References Cited

U.S. PATENT DOCUMENTS

| | | | | |
|---|---|---|---|---|
| 4,253,949 A | | 3/1981 | Hines et al. | |
| 4,780,415 A | * | 10/1988 | Ducellier et al. | 435/166 |
| 4,948,509 A | | 8/1990 | Stack | |
| 5,409,610 A | * | 4/1995 | Clark | 210/603 |
| 5,516,434 A | | 5/1996 | Cairo et al. | |
| 6,592,751 B2 | * | 7/2003 | Haridas | 210/97 |

* cited by examiner

*Primary Examiner*—Fred G. Prince
(74) *Attorney, Agent, or Firm*—Young & Thompson

(57) ABSTRACT

Method and apparatus for the anaerobic purification of slurry which contains organic constituents. Slurry which is to be treated is fed periodically or continuously to a mixture-filled, substantially closed reactor (2), while the slurry is forcibly mixed with mixture (3) from the reactor. The mixture in the reactor is subjected to upward flow through it and to a hydrolysis process. The mixture is subjected to floatation by injection of a low-oxygen gas, such as biogas which originates from the reactor, and the floating layer of solids which is formed in the process is returned to the mixture in the reactor, while the low-particle liquid which is formed in the process is discharged as effluent.

15 Claims, 1 Drawing Sheet

1
2
3
4
5
6
7
8
9
10
11
12
13
14
15
16
17
18
19
20
21
22
23
24
30
31

2
6
7
20
21

METHOD AND DEVICE FOR THE ANAEROBIC PURIFICATION OF A SLURRY WHICH CONTAINS ORGANIC CONSTITUENTS

CROSS-REFERENCE TO RELATED APPLICATION

This is the 35 USC 371 national stage of International Application PCT/NL02/00193 filed on 26 Mar. 2202, which designated the United States of America.

FIELD OF THE INVENTION

The present invention relates to a method for the anaerobic purification of slurry which contains organic constituents.

BACKGROUND OF THE INVENTION

It is known per se to use anaerobic purification in the treatment of waste water originating from the agricultural industry or from the foodstuffs industry. This is because of the presence of dissolved organic constituents, such as for example constituents originating from the processing of potatoes, vegetables, cereals, etc. In the known method, undissolved constituents are separated from the waste water which is to be subjected to anaerobic purification at an earlier stage by means of settling or floatation. However, a problem is that one still has to deal with the solid waste separated in a prior step. This so-called solid waste has to be discharged separately. Solid waste of this type is, for example, processed to form animal fodder. However, not all solid waste of this type is suitable for processing to form, for example, animal fodder and the market for processing into further products, such as for example animal fodder, may also stagnate.

SUMMARY OF THE INVENTION

It is an object of the present invention to provide a method in which the undissolved constituents, which are conventionally separated out beforehand, can also be treated.

According to the invention, this object is achieved by a method for the anaerobic purification of slurry which contains organic constituents, a) in which slurry which is to be treated is fed periodically or continuously to a mixture-filled, substantially closed reactor, b) in which the slurry is forcibly mixed with mixture from the reactor by subjecting the mixture in the reactor to an upward flow and a downward flow, c) in which the mixture in the reactor is subjected to a hydrolysis process, and d) in which the mixture from the reactor is subjected to flotation in a flotation cell by injection of a low-oxygen gas, such as biogas originating from the reactor, and the floating layer of solids which is formed is returned to the mixture in the reactor, and the low-particle liquid which is formed is discharged as effluent.

The slurry which is to be treated will be forcibly mixed with the mixture in the reactor, by circulating the mixture comprising the slurry supplied in the reactor by subjecting the mixture to upward and downward flow. If appropriate, forced mixing may be carried out directly during the supply of the slurry, for example by generating the upward and/or downward flow at or with the supply of slurry. The result of this is that at least some of the undissolved constituents in the slurry can be made to dissolve in at least the mixture which is present in the reactor. The mixture in the reactor, to which, therefore, slurry to be treated is fed periodically or continuously, is purified anaerobically by means of a hydrolysis process in a reactor with upward and downward flow. This leads to biogases being released, comprising, inter alia, $CO_2$ and $CH_4$. The fact that the reactor is substantially closed means that these biogases will collect at the top of the reactor, i.e. above the mixture located therein. To obtain relatively clean, i.e. relatively low-particle effluent, the mixture is subjected to floatation in a floatation cell, during which process a floating layer of solids is formed, which will float on top of the fluid which is present in the floatation cell. In addition, heavier particles will be able to collect at the bottom of the floatation cell. In order not to disturb the environment required for anaerobic purification by means of hydrolysis in the reactor, use is made during floatation of a low-oxygen gas, preferably an oxygen-free gas. In addition, a gas of this type prevents explosions on contact with the biogas. According to the invention, it is possible in particular for the biogas which is released during the anaerobic purification and which collects in the top of the substantially closed reactor to be used as a very appropriate low-oxygen gas of this type. The floating layer of solids which forms on top of the fluid in the floatation cell is fed back to the mixture, in order to be subjected once again to an anaerobic purification process by hydrolysis in the said mixture. Moreover, when further slurry is supplied, these constituents will also once again be forcibly subjected to a mixing process and, in the process, will ultimately be converted into dissolved impurities which can be converted into, inter alia, methane gas by hydrolysis via the anaerobic purification. The method according to the invention in particular makes it eminently possible to clean very dirty slurry by anaerobic means, i.e. the method for anaerobic purification can be carried out with mixtures which have a very high COD (chemical oxygen demand) (in this context, the term very high is understood as meaning a COD of more than 20 000 mg/l). With such high CODs, there are many flocs comprising bacteria which can easily be made to float in the reactor, as the applicant has discovered.

In the method according to the invention, it is particularly advantageous if the flotation cell is a tank which is open at the top, is delimited by an upper rim and is positioned in the reactor, preferably in the mixture, with its upper rim at a height which is greater than or equal to the level of the mixture located in the reactor. This prevents mixture from being able to flow out of the reactor via the upper rim into the floatation cell. If the upper rim is at a higher level than the level of the mixture located in the reactor, this is even ruled out altogether. The floating layer can in turn relatively easily be pushed over the upper rim back into the mixture in the reactor.

According to the invention, the floatation can be carried out particularly advantageously if in step d), biogas originating from the reactor is pressurized and is dissolved under pressure in part of the effluent, and the white water obtained in this way, in order to bring about the flotation, is injected into the floatation cell in such a manner that the level in the flotation cell is higher than the level of the mixture in the reactor. Pressurizing the biogas, for example in what is known as a compression tank, and injecting it under pressure into a tapped stream of the effluent—or if appropriate mixing the biogas and the tapped stream and then pressurizing them together—results in an increase in the solubility of the biogas in the tapped stream of effluent and in expansion occurring during the injection into the floatation cell, on account of the absence of the relatively high pressure of, for example, 2 to 5 bar or higher. On account of this expansion, relatively large bubbles of biogas are formed in the white water. Furthermore, the excess pressure leads to fluid situated in the floatation cell being raised in such a manner that the level of this fluid can come to lie at a higher level than the level of the mixture in the reactor vessel.

With a view to achieving simple and reliable supply of mixture from the reactor to the floatation cell, it is advantageous, according to the invention, if the flotation cell is provided with a feed opening which opens out into the mixture and is preferably provided in the bottom of the flotation cell, and in which the biogas or white water is injected into the flotation cell via the feed opening in such a manner that, by an ejector action, mixture is entrained out of the reactor into the floatation cell.

The upward flow in the reactor for the anaerobic treatment processed by hydrolysis can advantageously be achieved, according to the invention, by injecting a liquid, such as for example an auxiliary liquid or effluent originating from the floatation cell, into the bottom of the reactor. In this case, it is important for the liquid to have a high alkalinity with a view to buffering of the pH in the hydrolysis reactor.

According to a further aspect, the present invention relates to a device for the anaerobic purification of a slurry which contains organic constituents, the device comprising:

- a substantially closed hydrolysis reactor of the type with upward and downward flow;
- feed and mixing means for feeding slurry to the reactor, preferably with forced mixing, and mixing slurry in the reactor with mixture which is already present in the reactor;
- a flotation cell which is positioned inside the reactor and is in fluid communication with the interior of the reactor via, on the one hand, a feed opening for feeding mixture originating from the reactor to the floatation cell and, on the other hand, a discharge opening for discharging the floating layer which is formed in the floatation cell during use from the floatation cell;
- a floatation-gas supply system for supplying a floatation gas, in particular a low-oxygen floatation gas, to the floatation cell.

The advantages of this device are substantially the same as the advantages of the method according to the invention as have been explained above.

For reasons described above, the floatation-gas feed system of the device according to the invention advantageously comprises a biogas tapping line for tapping biogas from the top of the reactor, and pumping means for injecting the biogas into the floatation cell via an injection opening. For reasons which have already been explained above, it is advantageous, in the device according to the invention, if the floatation-gas supply system is designed in accordance with claim 8 of the application.

In the device according to the invention, the feed and mixing means can be produced in an advantageous way if they comprise at least one upwardly running pipe which is arranged in or along the tank and the upper end of which, during operation, is at a lower level than the level of the mixture in the reactor, and if the pipe is provided with a mixer which, during operation, generates a downward flow through the pipe, the pipe being provided, at the bottom end, with an outlet opening, and a slurry feed line opening out into the pipe. This creates a mixing chamber in which the slurry is fed to the reactor, in which mixing chamber well-controlled forced mixing with mixture from the reactor can take place. In order, on the one hand, to ensure that mixture is supplied from the reactor and, on the other hand, slurry which has been mixed with this mixture is discharged to the mixture in the reactor, the pipe is open at its upper end, and the mixer is designed in such a manner that it generates a downward flow through the pipe, and the pipe is open at the bottom end, in order for it to be possible for a downward flow to be discharged from the pipe. The downward flow also effects recirculation of the mixture in the reactor, since this mixture will be subjected to upward flow in the reactor and has to be fed back to the bottom for renewed treatment.

BRIEF DESCRIPTION OF THE DRAWINGS

The invention will be explained in more detail below with reference to an exemplary embodiment which is diagrammatically depicted in the drawing, in which.

DETAILED DESCRIPTION OF THE INVENTION

Figure 2:
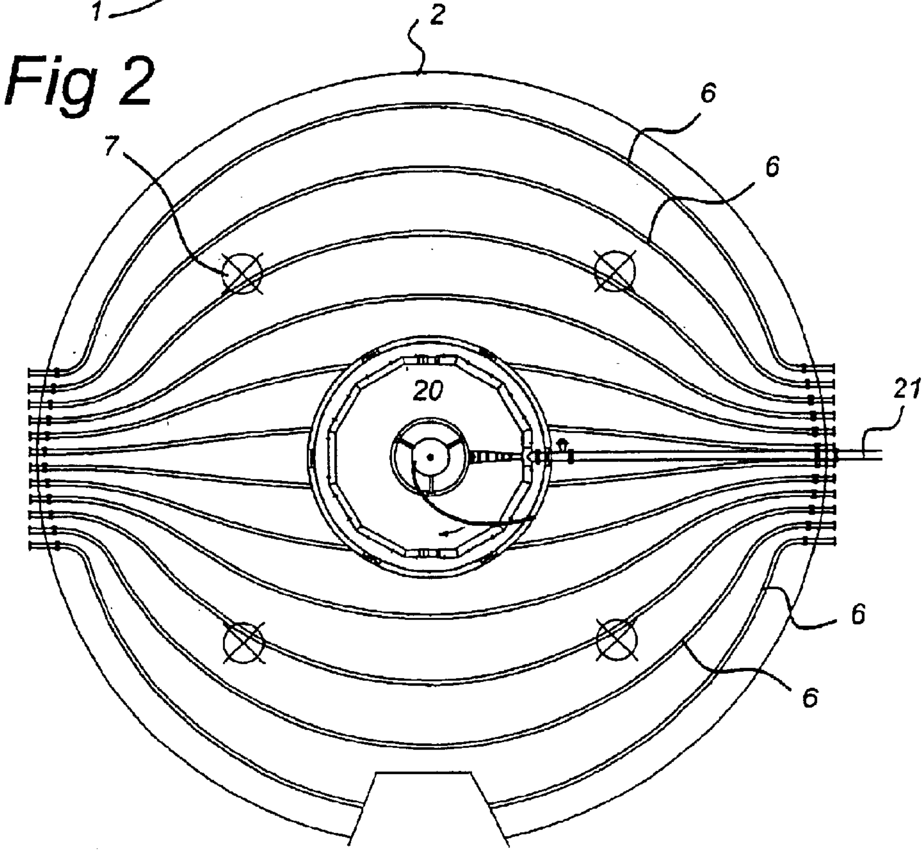
FIG. 2 shows a diagrammatic plan view of the device shown in FIG. 1.

The device 1 according to the invention comprises a reactor vessel 2 through which there is an upward flow. At least during operation, this reactor vessel 2 contains a mixture 3 with a liquid level 4 and, during operation, biogas, in particular comprising methane ($CH_4$) and $CO_2$, accumulates in the top of the reactor, i.e. above the level 4. The biogas is denoted by reference numeral 5. Since the biogas 5 can collect in the top of the reactor 2, it is important for the reactor 2 to be substantially closed. To effect an upward flow of the mixture 3 in the reactor vessel 2, a set of pipes 6, which can be seen particularly clearly from FIG. 2, is laid at the bottom of the reactor vessel 2. These pipes 6 are provided along their length with an outlet opening, via which liquid which is fed through the pipes 6, such as slurry or in particular what is known as dilution water, can be blown into the reactor. In the reactor there is a number of pipes 7, in the exemplary embodiment shown in the drawing four pipes 7. At least during operation, these pipes 7 are completely submerged in the mixture 3. The pipes 7 are open at the top side and are likewise open, or at least provided with outlet openings, at the underside. Also, in each of the pipes there is an agitator member 18 which is driven from outside the reactor via a shaft 9. The agitator member and the drive device are arranged in such a manner that, as a result, a downward flow is generated in the pipe, as a result of which mixture 3 is sucked out of the reactor 2 at the top side, as indicated by arrows, in order then to be blown back out of the pipe 7 at the underside. These pipes 7 and mixing members 8 thereby make it possible, if desired, although this is frequently not required, for the mixture 3, which, as indicated by arrow 10, is generally subjected to upward flow in the reactor vessel 2, to be returned to the bottom of the reactor 2. Furthermore, feed lines 8 for feeding slurry which is to be treated into the pipes 7 open out into the pipes 7. By then ensuring that, during the supply of the slurry, the agitators 8 are in operation, it is ensured that the slurry is forced to mix with the mixture 3 even while it is being fed into the reactor vessel 2. As a result, it will be possible to force some of the undissolved constituents in the slurry to dissolve. During operation, the slurry 8 will generally be supplied periodically or continuously. While the slurry is being supplied, the agitator members 18 will be in operation. If the supply of slurry 8 is shut down, the mixing members 18 will generally be switched off, but as indicated above the agitator members 18 may continue to operate or possibly may be kept operating temporarily or at least set in operation temporarily, for example for circulating mixture through the reactor.

Figure 1:
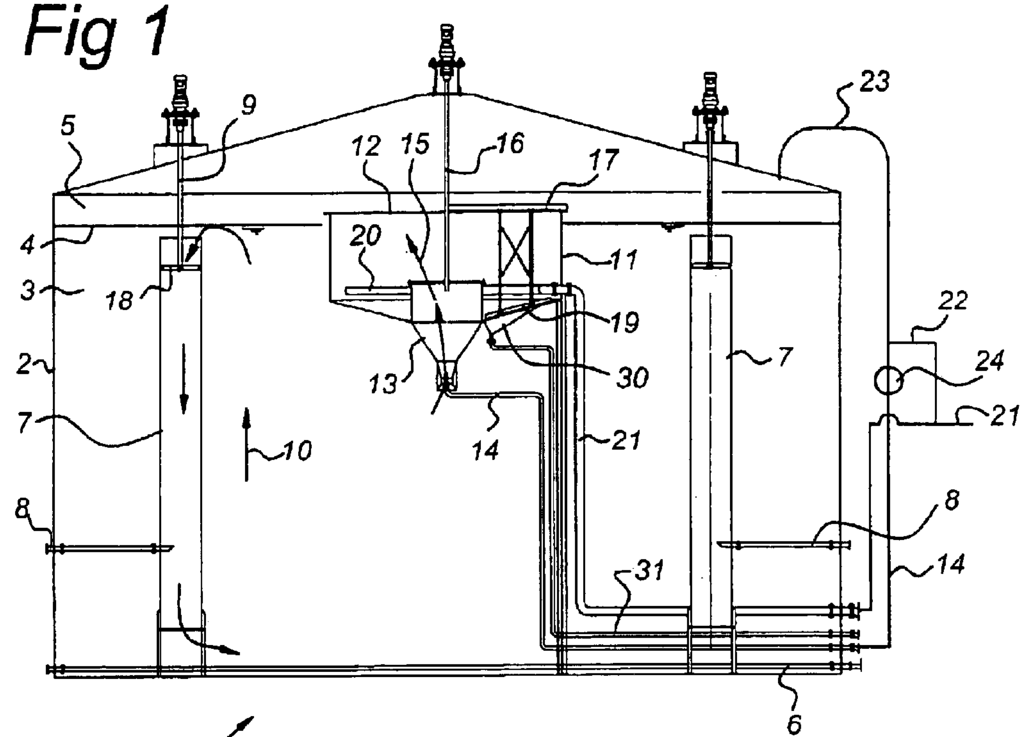
FIG. 1 shows a diagrammatic side view, in section, of a device according to the invention in which the method according to the invention is operated.

Since slurry with undissolved constituents is fed to the reactor, and it is undesirable for undissolved constituents of this type to be present in the effluent which is ultimately to be discharged from the reactor, a floatation cell 11 is arranged in the reactor 2. The floatation cell 11 comprises a tank which is substantially open at the top. At the top side, the open side of the tank 11 is delimited by an upper rim 12. As can be seen from FIG. 1, this upper rim 12 is higher than the level 4 of the mixture 3 in the reactor vessel 2. A conical inflow opening 13 is provided at the underside of the floatation cell 11. A white-water feed line 14 opens out into the inflow opening 13. As can also be seen from FIG. 1, the location where the white-water feed line 14 ends in the feed opening 13 is designed in venturi form. The result is that when the white water is injected via the line 14, an ejector action is brought about which, as indicated by arrow 15, ensures that mixture 3 is entrained out of the reactor vessel 2 into the floatation cell 11.

In the floatation cell 11, there is also a top clearing member 17, which is driven by a shaft 16, and a bottom clearing member 19. The top clearing member 17 is designed in such a way that it pushes what is known as the floating layer at the top of the floatation cell 11 over the rim 12 back to the mixture 3 in the reactor vessel 2. In this way, this floating layer, which substantially contains undissolved constituents, is returned to the process in the reactor vessel 2 for further treatment. The floating layer will in particular continue to float on top of the mixture 3 and then, when the agitator members 18 start to operate again, can be moved downwards via the pipes 7, with forced mixing. The bottom clearing member 19 pushes relatively heavy particles which have collected at the bottom to a recessed collection space 30, from which this sludge is discharged via line 31.

In the floatation cell 11 there is also an annular effluent-discharge line 20 which discharges effluent from the reactor via a central discharge line 21. The line 21 is provided with a branch 22 in order for effluent to be tapped off and to be mixed with biogas which is tapped off from the top of the reactor vessel via line 23. 24 denotes a compression tank in which the mixture of biogas and effluent is pressurized in order for this mixture, which is known as white water, then to be fed under pressure, via line 14, to the floatation cell 11 as floatation liquid.

What is claimed is:

1. Method for the anaerobic purification of slurry containing organic constituents, which comprises the steps of:

(a) periodically or continuously feeding the slurry to a mixture-filled, substantially closed reactor;

(b) forcibly mixing the slurry with mixture from the reactor by subjecting the mixture in the reactor to an upward flow and a downward flow;

(c) subjecting the mixture in the reactor to a hydrolysis process;

(d) subjecting the mixture to flotation in a flotation cell by injection of a biogas so as to form a floating layer of solids, and a low-particle liquid;

(e) returning the floating layer of solids to the mixture in the reactor; and (f) discharging the low-particle liquid as effluent.

2. The method according to claim 1, wherein the biogas used in step (d) originates from the reactor.

3. The method according to claim 1, wherein the flotation cell is a tank which is open at the top, is delimited by an upper rim and is positioned in the reactor, with its upper rim at a height which is greater than or equal to the level of the mixture located in the reactor.

4. The method according to claim 3, wherein in step (d), biogas originating from the reactor is pressurized and is dissolved under pressure in part of the effluent, and the white water obtained in this way, in order to bring about the flotation, is injected into the flotation cell in such a manner that the level in the flotation cell is higher than the level of the mixture in the reactor.

5. The method according to claim 3, wherein the flotation cell is provided with a feed opening which opens out into the mixture, and the biogas or white water is injected into the flotation cell via the feed opening in such a manner that, by an ejector action, the mixture is entrained out of the reactor into the flotation cell.

6. The method according to claim 5, wherein the feed opening opens out into the mixture at the bottom of the flotation cell.

7. The method according to claim 1, wherein the upward flow in the reactor is generated by injecting a liquid into the bottom of the reactor.

8. The method according to claim 7, wherein the injected liquid is effluent originating from the flotation cell, and having a high alkalinity.

9. The method according to claim 1, wherein the flotation cell is a tank which is open at the top, is delimited by an upper rim and is positioned in the mixture in the reactor, with its upper rim at a height which is greater than or equal to the level of the mixture located in the reactor.

10. Device for the anaerobic purification of a slurry which contains organic constituents, the device comprising:

a substantially closed hydrolysis reactor having upward and downward flow;

feed and mixing means for feeding slurry to the reactor, and mixing slurry in the reactor with mixture which is already present in the reactor;

a flotation cell which is positioned inside the reactor and is in fluid communication with the interior of the reactor via a feed opening for feeding mixture originating from the reactor to the flotation cell, and via a discharge opening for discharging from the flotation cell a floating layer which is formed in the flotation cell during use; and a flotation gas supply system for supplying a flotation gas to the flotation cell.

11. The device according to claim 10, wherein the flotation gas supply system comprises a biogas tapping line for tapping biogas from the top of the reactor, and pumping means for injecting the biogas into the flotation cell via an injection opening.

12. The device according to claim 11, wherein the flotation gas supply system also comprises an effluent tapping line which opens out into the flotation cell, and is in communication with the biogas tapping line, in order jointly to lead as a white water supply line to the injection opening.

13. The device according to claim 11, wherein the injection opening is positioned in such a manner with respect to the feed opening of the flotation cell, that with the feed opening located in the mixture during use, during injection of biogas or white water, an ejector action is generated, which entrains mixture from the reactor into the flotation cell.

14. The device according to claim 11, wherein the flotation cell is a tank which is open at the top and is delimited by a peripheral rim, and the pumping means feed biogas or white water to the flotation cell under a pressure which is such that, during use, the level in the flotation cell can reach a height which is higher than the level of the mixture in the reactor, which height is determined by the peripheral rim.

15. The device according to claim 10, wherein the feed and mixing means comprise at least one upwardly running pipe arranged in or along the tank and having an upper end, which during operation, is at a lower level than the level of the mixture in the reactor; the pipe being provided with a mixer, which during operation, generates a downward flow through the pipe, and also being provided at the bottom end with an outlet opening; and a slurry feed line opening out into the pipe.

* * * * *